United States Patent [19]

Wilson et al.

[11] 4,210,645

[45] Jul. 1, 1980

[54] (1,4)DITHIINO (2,3-b)(1,2,5)-THIADIAZOLE(3,4-e)PYRAZINE-6,7-DICARBONITRILE

[75] Inventors: Charles A. Wilson; Craig E. Mixan, both of Midland, Mich.

[73] Assignee: The Dow Chemical Company, Midland, Mich.

[21] Appl. No.: 894,670

[22] Filed: Apr. 10, 1978

[51] Int. Cl.$^2$ .................. A61K 31/505; C07D 513/14
[52] U.S. Cl. ..................................... 424/250; 544/345
[58] Field of Search ........................ 544/345; 424/250

[56] References Cited

U.S. PATENT DOCUMENTS

| 3,761,475 | 9/1973 | Kurihara et al. | 544/345 |
| 3,829,425 | 8/1974 | Kurihara et al. | 544/345 |

*Primary Examiner*—Donald G. Daus
*Assistant Examiner*—James H. Turnipseed

[57] ABSTRACT

The novel compound (1,4)Dithiino(2,3-b) (1,2,5)-thiadiazole(3,4-e)pyrazine-6,7-dicarbonitrile, its method of use in the control and kill of bacteria and fungi, and compositions containing the novel compound as the active ingredient therein are claimed.

3 Claims, No Drawings

(1,4)DITHIINO(2,3-b)(1,2,5)-THIADIAZOLE(3,4-e)PYRAZINE-6,7-DICARBONITRILE

SUMMARY OF THE INVENTION

This invention concerns the new compound (1,4)Dithiino(2,3-b)(1,2,5)thiadiazole(3,4-e)pyrazine-6,7-dicarbonitrile, hereinafter alternatively referred to as "Compound", corresponding to the formula

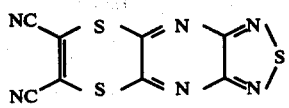

The Compound, directly or as the active ingredient in formulations and compositions, exhibits, in antimicrobially-effective amounts, antimicrobial activity against fungi and bacteria. Hereinafter the terms "antimicrobial" and "antimicrobially-effective", when used in conjunction with the Compound, will be employed to identify its activity against fungi and bacteria.

The Compound is prepared by adding 5,6-dichloro-1,2,5-thiadiazole(3,4-b)pyrazine to disodium dimercaptomaleonitrile in dimethylformamide (DMF) in accordance with the following equation:

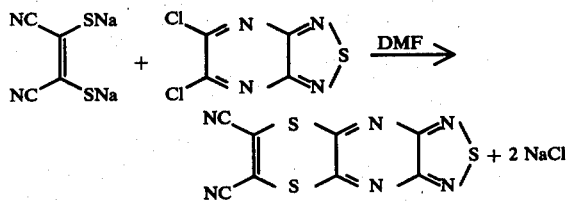

The reaction mixture is maintained at about 5° C. to about 50° C., and preferably from about 20° C. to about 30° C., with agitation until substantial completion of the reaction; usually from about 5 minutes to about 2 hours. Upon completion of the reaction, the resulting product mass is poured into ice water and allowed to stand for from about 5 minutes to about 3 hours, during which time the desired crude solid product precipitates. The product compound is recovered by filtration, washed with water and dried and, if desired, can be further purified by conventional techniques known to those skilled in the art.

Ordinarily substantial equimolar proportions of the starting materials are employed in the above-described process. However, any of the starting materials can be used in excess of the equimolar stoichiometric requirement.

DESCRIPTION OF THE PREFERRED EMBODIMENTS

The following example and teachings illustrate the present invention and the manner by which it can be practiced but as such should not be construed as limitations upon the overall scope of the same. The product Compound is identified by elemental analysis and nuclear magnetic resonance spectroscopy.

EXAMPLE

Preparation of (1,4)Dithiino(2,3-b)(1,2,5)-thiadiazole(3,4-e)pyrazine-6,7-dicarbonitrile To a stirred solution of 3.6 g (0.018 mole) disodium dimercaptomaleonitrile in 150 ml of dimethylformamide was added 3.6 g (0.017 mole) of 5,6-dichloro-1,2,5-thiadiazole(3,4-b)pyrazine. The reaction mixture was stirred at room temperature (~22° C.) for 5 minutes and was thereafter poured into 5000 ml of ice water. The resulting yellow solid precipitate which formed in about 5 minutes was collected by suction filtration, washed several times with water, and dried in vacuo to yield 4 g (85.3 percent yield from the pyrazine) of a light yellow solid; m.p. 250° C. (decomposition).

A sample was subjected to elemental analysis. The results obtained were as follows:

Analysis for $C_8N_6S_3$: Calcd.: C, 34.77; N, 30.42. Found: C, 33.86; N, 30.34.

Infra-red spectrophotometry confirmed the assigned structure.

The Compound of the invention is useful as an antimicrobial for the control of bacteria and fungi. This is not to suggest that the Compound and mixtures thereof with usual additives are equally effective against all such organisms at the same concentration. For such uses, the Compound can be employed in an unmodified form or dispersed on a finely divided solid and employed as a dust. Such mixtures can also be dispersed in water with the aid of a surface-active agent and the resulting emulsion employed as a spray. In other procedures, the Compound can be employed as the active constituent in solvent solutions, oil-in-water or water-in-oil emulsions. The augmented compositions are adapted to be formulated as concentrates and subsequently diluted with additional liquid or solid adjuvants to produce the ultimate treating compositions. Good control and kill have been realized against a number of representative compositions wherein antimicrobially-effective amounts of from about 5 to about 500 parts by weight of the Compound per million parts of such compositions are employed. As stated hereinbefore the active antimicrobially-effective amount to be employed against a given organism or in a certain composition can readily be determined by one skilled in the art.

Incorporation of the Compound of this invention into materials which are subject to fungal attack inhibits the growth of the fungi and preserves the original value of the materials. The compound is sufficiently nonvolatile and water-insoluble that it will persist on or in such materials for long periods of time. Examples of materials which are adversely affected by fungal growth are latex and alkyl paint films, wood and wooden products. The inventive Compound is sufficiently active against fungi such that only small quantities are required to prevent mildew on paint films or wood rot. The Compound is therefore useful for long-term protection against fungal growth in or on materials having a wood basis or a protective or decorative paint film subject to fungal attack.

In representative activity tests, a predetermined amount of the Compound is dispersed in warm melted nutrient agar which is then poured into a petri dish and allowed to solidify, the Compound being employed in an amount sufficient to provide from 5 to 500 parts by weight thereof per million parts (ppm) of the ultimate agar composition. The surface of the agar is then inoculated with a variety of bacterial and fungal pest organisms, and the inoculated plates are incubated under conditions conducive to bacterial and fungal growth.

In these studies, the Compound gave 100% growth inhibition (kills) and control of the following organisms at the indicated concentrations in parts per million:

TABLE

Antimicrobial Activity of (1,4)Dithiino(2,3-b)-(1,2,5)thiadiazole(3,4-e)pyrazine-6,7-dicarbonitrile

| Organism | Concentration in ppm |
|---|---|
| S. aureus | 50 |
| S. typhosa | 100 |
| B. subtilis | 5 |
| S. marcesens NIH | 500 |
| E. coli ATCC 11229 | 500 |
| C. albicans N | 50 |
| C. albicans D | 50 |
| C. pelliculosa | 5 |
| T. specie med. col. VI | 500 |
| A. pullulans | 50 |
| C. ips | 50 |
| T. mentagrophytes | 50 |

TABLE-continued

Antimicrobial Activity of (1,4)Dithiino(2,3-b)-(1,2,5)thiadiazole(3,4-e)pyrazine-6,7-dicarbonitrile

| Organism | Concentration in ppm |
|---|---|
| P. chryosgesum | 50 |
| Trichoderm Sp. P-42 | 50 |
| A. fumigatus | 50 |
| A. niger | 50 |

Preparation of the Starting Material 5,6-dichloro-1,2,5-thiadizaole(3,4-b)pyrazine may be prepared according to the method taught by Y. C. Tong, "1,2,5-Thiadiazole(3,4-b)pyrazines", *Journal of Heterocyclic Chemistry*, June 1975, vol. 12, pp. 451–453.

What is claimed is:

1. (1,4)Dithiino(2,3-b)(1,2,5)thiadiazole-(3,4-e)pyrazine-6,7-dicarbonitrile.

2. A method for controlling bacteria and fungi which comprises applying to said bacteria and fungi or their habitat an antimicrobially-effective amount of the compound of claim 1.

3. A composition for controlling bacteria and fungi comprising an antimicrobially-effective amount of the compound of claim 1 in combination with a solid or liquid diluent medium.

* * * * *